(12) United States Patent
Carlucci et al.

(10) Patent No.: US 6,362,390 B1
(45) Date of Patent: Mar. 26, 2002

(54) USE OF STAIN MASKING BACKSHEETS IN ABSORBENT ARTICLES

(75) Inventors: Giovanni Carlucci, Chieti; Maurizio Tamburro, Pescara, both of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/581,868

(22) PCT Filed: Dec. 9, 1998

(86) PCT No.: PCT/US98/26167

§ 371 Date: Jun. 19, 2000

§ 102(e) Date: Jun. 19, 2000

(87) PCT Pub. No.: WO99/30660

PCT Pub. Date: Jun. 24, 1999

(30) Foreign Application Priority Data

Dec. 18, 1997 (EP) ............................................. 97122344

(51) Int. Cl.$^7$ ................................................ A61F 13/15
(52) U.S. Cl. ................... 604/367; 624/385.01; 624/358
(58) Field of Search ............................ 604/385.01, 358, 604/362, 367, 375, 385.23

(56) References Cited

U.S. PATENT DOCUMENTS

| | | | | |
|---|---|---|---|---|
| 4,710,186 A | * | 12/1987 | DeRossett et al. | 604/383 |
| 4,801,494 A | * | 1/1989 | Datta et al. | 428/283 |
| 5,261,899 A | * | 11/1993 | Visscher et al. | 604/367 |
| 5,454,801 A | * | 10/1995 | Lauritzen | 604/378 |
| 6,140,551 A | * | 10/2000 | Niemeyer et al. | 604/367 |

* cited by examiner

*Primary Examiner*—John G. Weiss
*Assistant Examiner*—Jacqueline F Stephens
(74) *Attorney, Agent, or Firm*—Theodore P. Cummings; Kevin C. Johnson; Steven W. Miller

(57) ABSTRACT

The present invention relates to absorbent articles such as sanitary napkins and pantiliners and the use of backsheet constructions comprising a three dimensional formed film therein, to provide masking of the materials stored in the absorbent article when viewed through the garment facing surface of the absorbent article.

7 Claims, No Drawings

USE OF STAIN MASKING BACKSHEETS IN ABSORBENT ARTICLES

FIELD OF THE INVENTION

The present invention relates to absorbent articles such as sanitary napkins and pantiliners. In particular the present invention relates to the use of backsheet constructions within absorbent articles to provide masking of the materials stored within the article when viewed through the garment facing surface of the article.

BACKGROUND OF THE INVENTION

Absorbent articles such as sanitary napkins, diapers, incontinence products and perspiration pads are well known in the art. Typically these articles comprise a wearer facing surface and a garment facing surface. The wearer facing surface receives discharges from the body such as urine, faeces, vaginal discharges and the like which are to be absorbed and stored by the article. In order for the article to absorb the discharges the wearer facing surface of the articles needs to be liquid permeable. This wearer facing surface is known as the topsheet.

Topsheets are also well known in the art and are typically selected nonwovens, wovens or apertured film materials. Wovens and nonwovens are desirable in so far as they provide a clothlike appearance to the topsheet and appear relatively soft and comfortable to the wearer. However, the problem with such topsheets is that they also have some capacity to absorb. The topsheet thus rapidly becomes saturated and feels wet to the wearer of the product. Furthermore, such woven or nonwoven topsheets also rapidly develop a used, unclean and unsanitary appearance. Furthermore, the absorbed fluids are readily visible through the topsheet which is also considered unsightly and undesirable by consumers.

Attempts at remedying these problems have principally resided in providing the topsheet with surface treatments such as surfactants or fillers. However, neither of these treatments have resolved the problem satisfactorily. Alternatively it has also been proposed to provide alternative topsheet materials such as apertured formed films which have funnelled apertures which are designed to promote the passage of liquid discharge through the topsheet and into the absorbent core. These types of topsheet are preferred in that the problem of rewet is usually avoided. However, again these materials whilst reducing the visibility of the absorbed liquid contained in the absorbent core below do not entirely eliminate the problem.

In addition the problem of masking of the absorbed fluids and materials is not however merely limited to the stains from materials and fluids contained in the core which are visible when the product is viewed from or through the topsheet or the wearer facing surface of the article. Infact, this problem is also equally prevalent when the product is viewed from or through the backsheet or the garment facing surface where the absorbent fluids are also readily visible. Typically, these stains of the absorbed fluid in the absorbent core are particularly noticeable to the consumer of for example sanitary napkins or pantyliners as the article is removed from the undergarment and is folded for disposal. Again, it considered particularly undesirable to the consumers to view these stains as it appears that the absorbed material is in close contact to the undergarment and thus is unsanitary and that leakage may have occurred even if the absorbent capacity of the product has not been fully utilised.

A solution that has been proposed to address this problem and prevent the easy observation of stains through the backsheet material is simply to provide the backsheet or absorbent core with a coloured or non white appearance. However, coloured absorbent articles are unacceptable to consumers from an aesthetic standpoint, in particular because in contrast to white products coloured products are considered by many consumers to have a used and unsanitary appearance and are therefore undesirable.

Hence there still exists a need to provide masking of the absorbed materials contained within the absorbent core when viewed through the rear side or garment facing surface of the article without the necessity of utilising coloured article components.

It has now been surprisingly found that this problem may be addressed by the incorporation and use of a backsheet layer within an absorbent article wherein the backsheet comprises a three dimensional formed film layer.

SUMMARY OF THE INVENTION

The present invention relates to the use of a backsheet comprising a three dimensional formed film layer absorbent article, preferably a breathable absorbent article. Said article comprises a wearer facing surface and a garment facing surface and said backsheet comprises said garment facing surface. Accordingly, the present invention relates in particular to the use of said formed film layer to provide stain masking through said garment facing surface of said absorbent article.

DETAILED DESCRIPTION OF THE INVENTION

The present invention relates to absorbent disposable articles such as sanitary napkins, panty liners, incontinence products, perspiration pads and baby diapers. According to the present invention these products comprise a wearer facing surface, and a garment facing surface. Typically, such products comprise a liquid pervious topsheet providing the wearer facing surface, a backsheet providing the garment facing surface and an absorbent core intermediate said topsheet and said backsheet. The present invention relates to such articles which preferably comprise a moisture vapour permeable, liquid impervious backsheet more commonly referred to as a breathable backsheet.

The absorbent articles can also comprise any of the components or features usual in the art, in particular side wrapping elements, side flap components, or wings as well as any sort of extensibility or elastication feature can be comprised in absorbent articles. For example a typical sanitary napkin or panty liner comprises an adhesive area on the garment facing surface of the backsheet providing the panty-fastening adhesive which is covered by a release paper, wrapper or the like prior to the use of the article.

The absorbent article for absorbing liquid is described below by reference to a sanitary napkin or panty liner. However products such as adult or baby diapers, incontinence products or perspiration pads can similarly benefit from the present invention.

Backsheet

The absorbent article according to the present invention comprises as an essential feature a backsheet. The backsheet primarily prevents the extrudes absorbed and contained in the absorbent structure from wetting articles that contact the absorbent product such as underpants, pants, pyjamas and undergarments thereby acting as a barrier to fluid transport. The backsheet typically extends across the whole of the absorbent structure and can extend into and form part of, or all of the sideflaps, side wrapping elements or wings. In addition to acting as a liquid barrier, the backsheet of the present invention is also preferably breathable such that it permits the transfer of at least moisture vapour, preferably both vapour and air through it and thus allows the circulation of gases into and out of the backsheet.

It has now been further surprisingly identified that the utilisation of a backsheet comprising a three dimensional formed film layer also delivers desirable benefits in terms of masking of the material contained within the absorbent article. In particular, the use of a backsheet comprising a three dimensional formed film layer provides a reduction in the stain visible when the article is viewed from the garment facing surface.

The amount of absorbed fluid and material within the core that can be observed through the backing can be readily quantified by utilising the following as described herein. This test method utilises reflection spectrophotometric analysis to asses the basking ability of the backsheet construction in terms of whiteness and redness. Preferably the whiteness (L) parameter is greater than 70, more preferably greater than 75 and most preferably greater than 80 and the redness (a) parameter is preferably less than 5, more preferably less than 4, and most preferably less than 3.

According to the present invention suitable three dimensional formed films for use as backsheets to provide the benefits as described herein above may be any three dimensional formed film known in the art. The formed films may be apertured or non apertured. However, apertured formed film layers are particularly preferred due to their ability to provide breathability to the absorbent article.

Whilst not being bound by theory it is believed that the stain masking through the garment facing surface of the absorbent article provided by three dimensional films is achieved by a result of two principle effects. Firstly the typically utilised 2 dimensional films have a width of approximately only 20 to 30 micrometers and are thereby effectively transparent and allow the materials contained in the core to be readily observed In contrast the use of a 3-dimensional film within the backsheet construction creates by its very nature of protruding funnels an increased width between the core and the garment facing surface of the article of approximately 500 micrometers, at which the ability of the human eye to detect the materials contained in the core is considerably reduced. Secondly, the incorporation of 2-dimensional films within the backsheet construction also results in the some of the absorbed material in the core being smeared over the surface of the backsheet material with which the core comes in contact with. This again further accentuates the visibility of the absorbed materials through the backsheet. However, in contrast the use of 3-dimensional films of the present invention reduces the surface area contact between the core and the backsheet and as a result the absorbed material is not smeared across the surface of the backsheet. As a result of the combination of these effect the visibility of the absorbent materials through the garment facing surface of the absorbent articles is reduced.

Suitable apertured formed films for use herein include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured performed films are uni directional such that they have at least substantially, if not complete one directional fluid transport towards the core.

Other suitable formed film layers for use herein include macroscopically expanded films as described in for example in U.S. Pat. Nos. 4,637,819 and 4,591,523.

According to the present invention the backsheet may in addition to said three dimensional formed film layer comprising additional layers. Any layer known in the art as a suitable backsheet material may be effectively employed and includes wovens or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance.

In a preferred embodiment of the present invention the additional layers are also moisture vapour permeable and hence breathable. Suitable moisture vapour permeable layers include 2 dimensional, planar micro and macro-porous films, macroscopically expanded films, formed apertured films and monolithic films. According to the present invention the apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable 2 dimensional porous planar layers of the backsheet may be made of any material known in the art, but are preferably manufactured from commonly available polymeric materials. Suitable materials are for example Goretex™ or Sympatex™ type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours international S.A, Switzerland such as Pebax™, available from Elf Atochem (France) and Estane™ available from BF Goodrich (Belgium).

Preferred breathable backsheets for use herein are those having a high moisture vapour exchange, most preferably both a high moisture vapour and high air exchange. Particularly preferred backsheets for the present invention comprise at least two layers comprising said three dimensional apertured formed film and at least one additional layer selected from the above, such as a microporous layer or an apertured formed film a fibrous woven or nonwoven. The most preferred breathable backsheet component comprises a microporous film and an apertured formed film.

The Topsheet

According to the present invention the absorbent articles comprise a topsheet. The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and nonwoven materials; polymeric materials such as apertured formed thermoplastic films, apertured plastic films,, and hydroformed thermoplastic films; and thermoplastic scrims. Suitable woven and non woven materials can be comprised of natural fibers (e.g., wood or cotton fibers), synthetic fibers (e.g., polymeric fibers such as polyester, polypropylene, or polyethylene fibers) or from a combination of natural and synthetic fibers or bi-/multi-component fibers and are preferably hydrophobic.

Preferred topsheets for use in the present invention are selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred micro apertured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Ohio as "DRI-WEAVE".

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The wearer facing surface of the formed film topsheet can be hydrophilic so as to help liquid to transfer though the topsheet faster than if the body surface was not hydrophilic. In a preferred embodiment, surfactant is incorporated into the polymeric materials of the formed film topsheet such as is described in PCT-publication WO 93/09741. Alternatively, the body surface of the topsheet can be made hydrophilic by treating it with a surfactant such as is described in U.S. Pat. No. 4,950,254.

Another alternative are so called hybrid topsheets which incorporate fibrous and film like structures. Particularly useful embodiments of such hybrid topsheets are disclosed in PCT publications WO 93/09744; WO 93/11725 or WO 93/11726.

When referring to the topsheet a multi layer structure or a mono layer structure is contemplated. The hybrid topsheet mentioned above is such a multi layer design but other multi layer topsheets such as primary and secondary topsheet designs are also considered.

The topsheet typically extends across the whole of the absorbent structure and outside the area coextensive with the absorbent structure. The topsheet can extend and form part or all of the preferred side flaps, side wrapping elements or wings.

Absorbent Core

According to the present invention the absorbent cores suitable for use in herein may be selected from any of the absorbent cores or core system known in the art. As used herein the term absorbent core refers to any material or multiple material layers whose primary function is to absorb, store and distribute fluid.

According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components.

a Primary/Secondary Fluid Distribution Layer

One optional component of the absorbent core according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials usually referred to as "hydrogel", "superabsorbent", hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross-linked, partially neutralised, polymeric gelling material. This material forms a hydrogel upon contact with water. Such polymer materials can be prepared from polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent core according to the invention and preferably is provided close to or as part off the primary or secondary fluid distribution layer are odor control agents.

A preferred sanitary napkin or panty liner made according to the present invention has a pair of side wrapping elements or "undergarment covering components". These elements or components provide coverage of the wearer's panties to reduce side soiling (i.e., staining of the edges of the panty crotch) and are typically smaller than conventional flaps or wings.

The function of the side wrapping elements, whether integral with the article or joined to the article after being formed separately, is further improved by rendering them extensible in one or both directions parallel to the longitudinal axis and/or lateral axis. The extensibility can be provided across all or only part of the side wrapping elements and can be achieved by pleating or ring-rolling those parts which are to be rendered extensible.

According to the present invention the topsheet, backsheet and absorbent core components are joined together to provide the absorbent article. Typically, at least two, preferably all of the components of the article are joined to form the article. Each of said components of the absorbent article comprise at least one layer and have a wearer facing surface and a garment facing surface. Typically, adjacent garment facing surfaces form a common interface with the wearer facing surface of an adjacent component or layer. The elements or layers are joined together across this common interface. In this manner, the topsheet is joined to the absorbent core, and the core is joined to the backsheet. In addition, the topsheet may be directly or indirectly by joined to the backsheet at the periphery of the absorbent article. Furthermore, particularly in sanitary napkin, panty liner and incontinence product applications, the garment facing surface of the backsheet also provides the surface to which the absorbent article is releasably joined to the garment of the user of the product. Prior to use, this surface is typically provided with a protective cover. Any means known in the art to join the components of the absorbent article and provide the garment fastening. May be utilised such as utilising a continuous layer of adhesive, a patterned layer of adhesive, such as spirals, or spots, or using heat bonds, pressure bonds, mechanical bonds and the like.

Test Method

Backsheet Masking Test-Reflection Spectrophotometric Analysis

This test assesses the backsheet masking level (redness/whiteness) of a sanitary napkin following usage or by simulated loading of the pad with synthetic blood.

Apparatus

X-Rite colorimetric Mod: 948/968. This equipment measures spectral reflectance according to the Hunter Lab (L, a, b components) according to industry standard CIE1976.

Procedure: Laboratory Simulation of Masking:

1. In accordance with the manual procedure calibrate the calorimetric X-Rite.
2. Place a fresh pad on the laboratory bench with the wearer facing surface (topsheet) facing upwards.
3. Load 10 ml of synthetic blood onto the centre pad.
4. After 1 min. apply a pressure/weight of 60 g/sqcm on the pad.
5. Remove the weight and place the pad with garment facing surface (backsheet) facing upwards and remove the silicon paper.
6. Place the X-rite instrument on the backsheet and measure the Hunter L,a,b values. Take an average of 10 readings over the loaded area.
7. The test is repeated on 5 separate pads.

EXAMPLES

The masking test was carried out on modified sanitary napkins available under the trade name Always Ultra Normal, manufactured by Procter & Gamble, Germany, where the backsheet is replaced as indicated below.

Example 1

The backsheet is a white polyethylene film.

Example 2

The backsheet is a peach polyethylene film.

Example 3

The backsheet is a pink polyethylene film.

Example 4

The backsheet is a dual layer construction consisting of a 3-dimensional apertured formed film available from Tredagar film products, Holland under the code S225MD25 and a microporous polyethylene film available from Exxon Chemical Company, USA under the code XBF112W.

Example 5

The backsheet is a white polyethylene film as for example 1, which is not loaded with blood and is unused.

Results

| Example | 1 | 2 | 3 | 4 | 5 |
|---|---|---|---|---|---|
| Whiteness (L) | 68 | 61 | 69 | 89 | 96 |
| Redness (a) | 5.4 | 8.2 | 5.1 | 0.3 | 0.0 |

As can be seen example 4 which represents an embodiment of the present invention provides a significantly higher whiteness (L) parameter and significantly reduced redness (a) parameter which resemble the values for an unused napkin.

What is claimed is:

1. An absorbent article having a garment facing surface and a user facing surface, comprising:

a topsheet;

a backsheet positioned opposite of the topsheet;

an absorbent core positioned between the topsheet and the backsheet, the backsheet having a three dimensional formed film layer, the three dimensional formed film layer providing stain masking of stains through the garment facing surface of the absorbent article, the backsheet having a whiteness (L) parameter of greater than 70 and redness (a) parameter of less than 5 as measured in the backsheet masking test.

2. The absorbent article of claim 1 wherein the backsheet has a whiteness (L) parameter of greater than 75 and a redness (a) parameter of less than 4 as measured in the backsheet masking test.

3. The absorbent article of claim 1 wherein the backsheet is moisture vapor permeable and liquid impermeable.

4. The absorbent article of claim 1 wherein the backsheet is an apertured formed film.

5. The absorbent article of claim 1 wherein the topsheet comprises a hydrophobic nonwoven.

6. The absorbent article of claim 1 wherein the topsheet comprises an apertured polymeric film.

7. The absorbent article of claim 1 wherein the absorbent article is a sanitary napkin or panty liner.

* * * * *